US00PP10064P

Jnited States Patent [19]

Iammett

[11] Patent Number: Plant 10,064

[45] Date of Patent: Oct. 14, 1997

[4] CHRYSANTHEMUM PLANT NAMED 'FLIRTATION'

[6] Inventor: Keith Richard William Hammett, 488c Don Buck Road, Massey, Auckland 8, New Zealand

[1] Appl. No.: 647,291

[2] Filed: May 9, 1996

[1] Int. Cl.[6] ..... A01H 5/00

[2] U.S. Cl. ..... Plt./74.1

[8] Field of Search ..... Plt./74.1, 82.4

[6] References Cited

U.S. PATENT DOCUMENTS

P.P. 8,756 5/1994 VandenBerg ..... Plt./74.1

OTHER PUBLICATIONS atta, 1994, "Sensitivity of mutant genotypes of chrysanemum to gamma rays", J. Nuclear Agric. Biol. (4):251–254.

atta, et al., 1994, "Analysis of floret characters in chrynthemum mutants", J. Nuclear Agric. Biol. (3):146–147.

Shankar, et al., 1993, "Evaluation of chrysanthemum (Chrysanthemum morifolium Ram.) cultivars with special reference to their morphological characters", Bioved 4(1):53–56.

Datta et al., 1994, "Micromorphological studies of original and mutant cultivars of ornamentals", Feddes Repertorium 105(3–4):167–174.

Datta, 1987, "'Man Bhawan'–new chrysanthemum cultivar induced by gamma irradiation", J. Nuclear Argic. Biol. 16:217–218.

Mesi, 1984, "New cultivars of chrysanthemum", Indian Horticulture 29(1):19–20.

*Primary Examiner*—Howard J. Locker
*Attorney, Agent, or Firm*—C. A. Whealy

[57] ABSTRACT

A distinct cultivar of Chrysanthemum plant named Flirtation, characterized by its flat capitulum form; moderately vigorous and short growth habit; freely branching plant habit; small daisy-type inflorescences; soft pink ray florets; numerous inflorescences per plant; and good garden performance.

1 Drawing Sheet

The present invention relates to a new and distinct cultivar Chrysanthemum plant, botanically known as *Dendranema grandiflora* and referred to by the cultivar name irtation.

The new cultivar is a product of a planned breeding ogram conducted by the inventor in Massey, Auckland, ew Zealand. The objective of the breeding program was to eate new Chrysanthemum cultivars having a fast flowering sponse, desirable inflorescence colors, and good garden rformance.

The new cultivar originated from a open pollination of the rysanthemum cultivar Magic Dream (not patented) as the nale or seed parent with the male or pollen parent which is either the Chrysanthemum cultivar Magic Sunset, agic Dawn or Magic Garden (all nonpatented). The actual ossing was effected by pollinating insects.

The cultivar Flirtation was discovered and selected by the ventor as a flowering plant within the progeny of the stated oss in a controlled environment in Massey, Auckland, New aland.

Asexual reproduction of the new cultivar by terminal ttings taken at Massey, Auckland, New Zealand, has own that the unique features of this new Chrysanthemum stable and reproduced true to type in successive generans.

The following traits have been repeatedly observed and determined to be the unique characteristics of Flirtation. ese characteristics in combination distinguish Flirtation a new and distinct cultivar:

1. Flat capitulum form.
2. Moderately vigorous and short growth habit.
3. Freely branching plant habit.
4. Small daisy-type inflorescences.
5. Soft pink ray florets.
6. Numerous inflorescences per plant.
7. Good garden performance.

The cultivar Flirtation has not been observed under all possible environmental conditions. The phenotype may vary somewhat with variations in environment such as temperature, daylength and light intensity, without, however, any variance in genotype.

In side-by-side comparisons in Massey, Auckland, New Zealand, under commercial practice, plants of the new Chrysanthemum have more ray florets, larger inflorescences, and flower 10 days earlier than the female parent, the Chrysanthemum cultivar Magic Dream. Additionally, the ray floret color of the Chrysanthemum cultivar Magic Dream is dark purple compared to the soft pink ray floret color of the new Chrysanthemum. In the same comparisons, plants of the new Chrysanthemum differ from the probable male parents in ray floret color. The cultivar Magic Sunset has crimson ray florets, the cultivar Magic Dawn has light yellow ray florets and the cultivar Magic Garden has yellow ray florets compared to the soft pink ray floret color of the new Chrysanthemum. Additionally, plants of the cultivars Magic Sunset and Magic Dawn have fewer ray florets per inflorescence than plants of the new Chrysanthemum.

Plants of the new Chrysanthemum are similar to the cultivar Megan (U.S. Plant Pat. No. 8,756) in ray floret color. However, in side-by-side comparisons conducted in Oxnard, Calif., under commercial practice, plants of the new Chrysanthemum differed from plants of the cultivar Megan in the following characteristics:

1. Plants of the new Chrysanthemum are taller and have longer lateral stems than plants of the cultivar Megan.
2. Plants of the new Chrysanthemum have more leaves per lateral stem than plants of the cultivar Megan.
3. Leaves of plants of the new Chrysanthemum are larger than leaves of plants of the cultivar Megan.
4. Inflorescences of plants of the new Chrysanthemum are larger than inflorescences of plants of the cultivar Megan.
5. Ray florets of plants of the new Chrysanthemum are larger than ray florets of plants of the cultivar Megan.

6. Plants of the new Chrysanthemum have fewer ray florets but more disc florets per inflorescence than plants of the cultivar Megan.

7. Peduncles of plants of the new Chrysanthemum are longer and stronger than peduncles of plants of the cultivar Megan.

8. The peduncle angle of plants of the new Chrysanthemum is more obtuse than the peduncle angle of plants of the cultivar Megan.

A detailed comparison of plants of the new Chrysanthemum and the cultivar Megan appears in Chart A at the end of the specification.

The accompanying colored photograph illustrates the overall appearance of the new cultivar, showing the colors as true as it is reasonably possible to obtain in colored reproductions of this type. The photograph comprises a top perspective view of a typical flowering 16.5-cm container of Flirtation with three cutting in the container.

In the following description, color references are made to the Royal Horticultural Society Colour Chart except where general terms of ordinary dictionary significance are used. The following observations and measurements describe plants grown in Oxnard, Calif. under commercial practice in a glass-covered greenhouse with average night temperatures of 18C, average day temperatures of 30C, and light levels of 2,000 (cloudy conditions) to 9,000 (sunny conditions) foot-candles.

After sticking unrooted cuttings of the new cultivar, plants received 21 long day/short nights followed by short day/long nights until flowering. Measurements and numerical values represent ranges or averages for six typical flowering plants.

Botanical classification: *Dendranthema grandiflora* cultivar Flirtation.

Commercial classification: Garden chrysanthemum.

Parentage:

*Female, or seed, parent.*—*Dendranthema grandiflora* cultivar Magic Dream (not patented).

*Male, or pollen, parent.*—Either *Dendranthema grandiflora* cultivar Magic Sunset, Magic Dawn or Magic Garden (all nonpatented).

Propagation:

*Type.*—Terminal tip cuttings.

*Time to rooting.*—9 to 11 days with soil temperatures of 21C.

*Rooting habit.*—Fine, fibrous and well-branched.

Plant description:

*Appearance.*—Perennial herbaceous decorative garden plant. Stems upright, uniform habit and freely branching. Moderately vigorous and compact growth habit.

*Plant height.*—About 23 cm.

*Lateral branch length.*—About 20 cm.

*Quantity of lateral branches after removal of apical meristem.*—About 5.

*Stem color.*—147B.

*Foliage description.*—Number of leaves per lateral branch: About 16. Leaf arrangement: Alternate. Leaf size, fully expanded: Length: About 6.5 cm. Width: About 3.8 cm. Leaf apex: Acuminate. Leaf base: Attenuate. Leaf margin: Palmately lobed. Leaf texture: Upper and under surfaces slightly pubescent, smooth and dull. Veins prominent on under surface. Petiole length: About 1 cm. Color: Young foliage upper surface: 147A. Young foliage under surface: 147B. Fully expanded foliage upper surface: 147A. Fully expanded foliage under surface: 147B. Venation upper surface: 147B. Venation under surface: 147B. Petiole: 147A.

Flowering description:

*Appearance.*—Daisy inflorescence form. Inflorescences borne on terminals above foliage, arising from leaf axils. Disc and ray florets arranged acropetally on a flat capitulum.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to 2 to 3 weeks of long day/short night conditions after sticking followed by photoinductive short day/long night conditions, flower about 55 to 59 days later.

*Quantity of Inflorescences.*—About 5 inflorescences per flowering stem.

*Inflorescence size.*—Diameter: About 5.5 cm. Depth (height): About 1 cm. Diameter of disc: About 1.6 cm.

*Ray Florets.*—Shape: Short, broad. Size: Length: About 2.5 cm. Width: About 1.4 cm. Apex: Dentate. Base: Acute. Margin: Entire. Texture: Satiny, smooth and glabrous. Aspect: Flat. Number of ray florets per inflorescence: About 32. Color: When opening, upper surface: 75A/75B. When opening, under surface: 75A. Mature, upper surface: 69A, fading to very light pink with subsequent development. Mature, under surface: 155D.

*Disc florets.*—Shape: Tubular. Size: Length: About 6 mm. Width: About 1 mm. Number of disc florets per inflorescence: About 130. Color: Immature: 154A. Mature: 13A.

*Peduncle.*—Aspect: Strong and angled about 40° to the stem. Length: About 9 cm. Texture: Glabrous. Color: 147B.

*Reproductive organs.*—Androecium: Present on disc florets only. Anther color: 13A. Pollen: Moderate, 13A in color. Gynoecium: Present on both ray and disc florets. Style color: 154C.

Disease resistance: High tolerance to Brown Rust, *Puccinia chrysanthemi* Roze., has been observed on plants grown under commercial greenhouse conditions.

Seed production: Seed production has not been observed.

CHART A

| CHARACTERISTIC | FLIRTATION | MEGAN |
|---|---|---|
| PLANT HEIGHT | About 23 cm | About 20 cm |
| LATERAL STEM LENGTH | About 20 cm | About 16 cm |
| QUANTITY OF LEAVES PER LATERAL STEM | About 16 | About 14.5 |
| LEAF LENGTH | About 6.5 cm | About 4.5 cm |
| LEAF WIDTH | About 3.8 cm | About 2.5 cm |
| INFLORESCENCE DIAMETER | About 5.5 cm | About 4 cm |
| INFLORESCENCE HEIGHT | About 1 cm | About 0.8 cm |
| RAY FLORET LENGTH | About 2.5 cm | About 1.7 cm |

-continued

CHART A

| IARACTERISTIC | FLIRTATION | MEGAN |
|---|---|---|
| \Y FLORET WIDTH | About 1.4 cm | About 0.5 cm |
| \Y FLORET COLOR, HEN OPENING, UPPER SIDE | 75A/75B | 75A/75B |
| \Y FLORET COLOR, MATURE, PPER SIDE | 69A | 69A |
| \Y FLORET COLOR, MATURE, NDER SIDE | 155D | 69C |
| JMBER OF RAY FLORETS PER FLORESCENCE | About 32 | About 70 |
| JMBER OF DISC FLORETS PER FLORESCENCE | About 130 | About 62 |

-continued

CHART A

| CHARACTERISTIC | FLIRTATION | MEGAN |
|---|---|---|
| DIAMETER OF DISC | About 1.6 cm | About 0.9 cm |
| PEDUNCLE LENGTH | About 9 cm | About 5 cm |
| PEDUNCLE STRENGTH | Strong | Weak |
| PEDUNCLE ANGLE TO STEM | About 40° | About 30° |

It is claimed:

1. A new and distinct cultivar of Chrysanthemum plant named Flirtation, as illustrated and described.

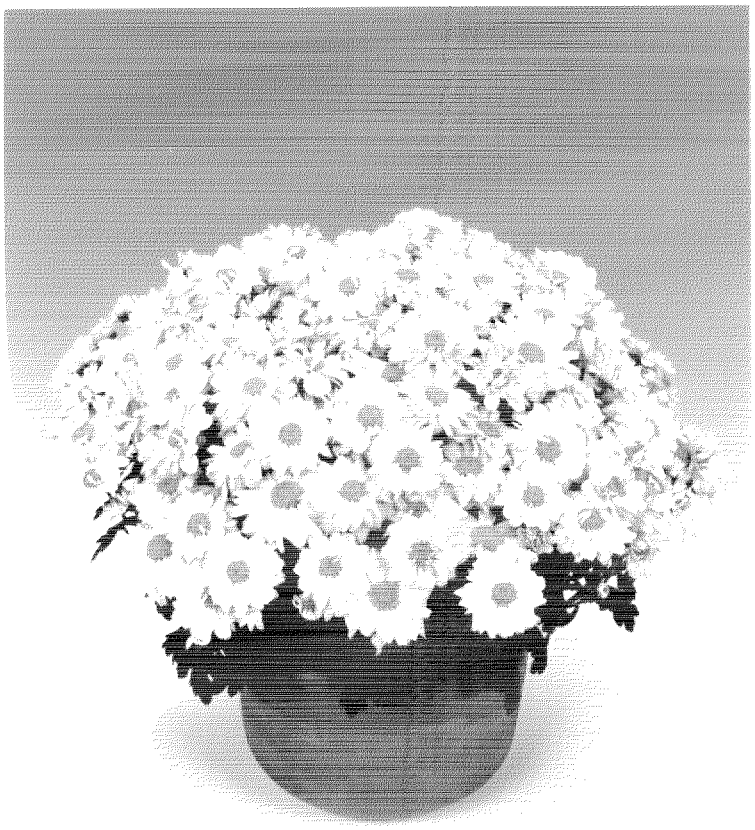

* * * * *